United States Patent
Cullis-Hill

(10) Patent No.: US 6,593,310 B1
(45) Date of Patent: Jul. 15, 2003

(54) TREATMENT OF OSTEOPOROSIS

(75) Inventor: David Cullis-Hill, Sydney (AU)

(73) Assignee: Arthropharm Pty. Ltd., New South Wales (AU)

( * ) Notice: Subject to any disclaimer, the term of this patent is extended or adjusted under 35 U.S.C. 154(b) by 70 days.

(21) Appl. No.: 09/716,818

(22) Filed: Nov. 21, 2000

(51) Int. Cl.$^7$ ............................................. A61K 31/715
(52) U.S. Cl. ........................ 514/54; 514/169; 514/171
(58) Field of Search ........................ 514/54, 169, 171

(56) References Cited

PUBLICATIONS

Derwent Abstract, 199348, 1993.*

* cited by examiner

*Primary Examiner*—Zohreh Fay
(74) *Attorney, Agent, or Firm*—Nixon & Vanderhye

(57) ABSTRACT

A method for treating osteoporosis which comprises administering to a mammal in need of such treatment an effective amount, typically in the range of 0.1 to 100 micrograms per kg of body weight, of a compound capable of maintaining the integrity of connective tissue, for example pentosan polysulfate.

Structural formula of pentosan polysulfate (PPS) isolated from beechwood hemicellulose (*Fagus silvatica*). This formula shows that the linear xylan (pentosan) backbone of pentosan polysulfate contains on average one 4-O-methylglucuronate side chain linked to the 2-position on every tenth xylose (pentose) ring. The calcium derivative of PPS (CaPPS) is when $R=SO_3^-Ca^{+}\frac{1}{2}$.

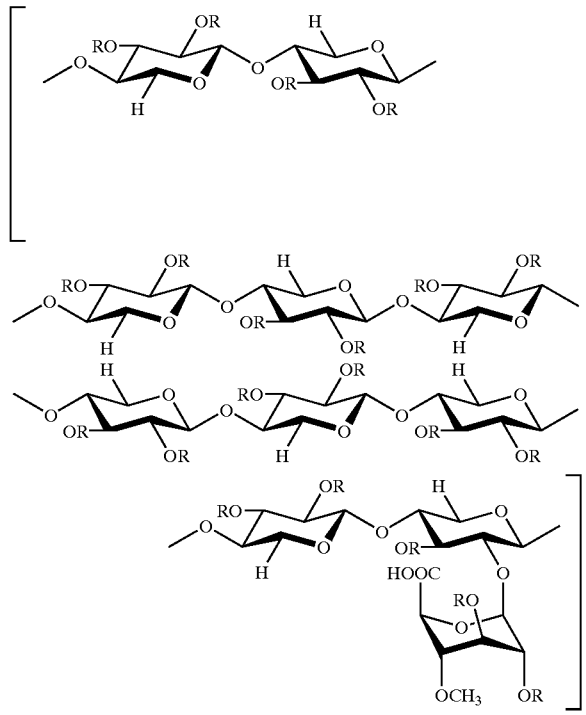

23 Claims, No Drawings

TREATMENT OF OSTEOPOROSIS

The present invention relates to methods for treatment of bone disorders. More particularly, the invention provides a method for treating bone disorders, particularly osteoporosis, using low doses of polysulfated polysaccharides, for example calcium pentosan polysulfate.

BACKGROUND OF THE INVENTION

Osteoporosis is a systemic skeletal disease, characterized by low bone mass and deterioration of bone tissue, with a consequent increase in bone fragility and susceptibility to fracture. It is the most common type of metabolic bone disease in the U.S., and the condition affects more than 25 million people. The disease causes more than 1.3 million fractures each year, including 500,000 spine, 250,000 hip and 240,000 wrist fractures annually. Hip fractures are the most serious consequence of osteoporosis, with 5–20% of patients dying within one year, and over 50% of survivors being incapacitated.

Osteoporosis literally means "porous bones". The bones in the skeleton are made of a thick outer shelf and a strong inner mesh filled with collagen (protein), calcium salts and other minerals. The inside has the appearance of a honeycomb, with blood vessels and bone marrow in the spaces between bone. Osteoporosis occurs when the holes between bone become bigger, making it fragile and liable to break easily. Osteoporosis usually affects the whole skeleton but it most commonly causes breaks (fractures) to bone in the wrist, spine and hip. Old bone is broken down by cells called osteoclasts and replaced by bone building cells called osteoblasts. This process of renewal is termed bone turnover.

The elderly are at greatest risk of osteoporosis. The problem is therefore predicted to increase significantly with the aging of the population. Worldwide fracture incidence is predicted to increase three-fold over the next 60 years.

There are a number of causes of osteoporosis. Hormone deficiencies (estrogen in women and androgen in men) are the leading cause. It is well known that women are at greater risk of osteoporosis than men. Women experience a sharp acceleration of bone loss during the five years following menopause. Other factors which increase the risk include smoking, alcohol abuse, a sedentary lifestyle and low calcium intake.

There are various therapies available for post-menopausal osteoporosis. The most common are hormone replacement therapy (HRT), bisphosphonates and calcitonin. These three treatments work as anti-resorptive agents. Other adjuncts to these therapies may be recommended, including adequate calcium intake, vitamin D and weight bearing exercise. Other drugs may be used in conjunction with these therapies, including tamoxifen (commonly used as an adjunct in the treatment of breast cancer), thiazide diuretics (used in the treatment of hypertension) and sodium fluoride which is presently undergoing evaluation by the Food and Drug Administration in order to be approved for the treatment of osteoporosis.

Estrogen is known to reduce fractures, and is an example of an anti-resorptive agent. In addition, Black, et al. (EP 0605193A1) report that estrogen, particularly when taken orally, lowers plasma levels of low density lipoproteins (LDL's) and raises those of the beneficial high density lipoproteins (HDL's). However, estrogen failed to restore bone back to young adult levels in the established osteoporotic skeleton. Moreover, long-term estrogen therapy has been implicated in a variety of disorders, including an increase in the risk of uterine cancer, endometrial cancer and possibly breast cancer, causing many women to avoid this treatment. The significant undesirable effects associated with estrogen replacement therapy support the need to develop alternative therapies for osteoporosis that have the desirable effect on serum LDL but do not cause undesirable effects.

Bisphosphonates are non-hormonal treatments for osteoporosis which work by "switching off" the cells that break down bone, allowing the bone building cells to work more efficiently. There are three bisphosphonates available in the UK, alendronate (Fosamax), etidronate (Didronel PMO) and risedronate (Actonel). Didronel PMO and Fosamax are also licensed for the treatment of osteoporosis caused by corticosteroids and for the prevention of osteoporosis in women who have low bone mass (osteopenia). Fosamax is a new drug currently awaiting FDA approval. Studies show that the risk of spinal fracture in post-menopausal women treated with Fosamax are reduced by nearly 50%.

Calcium and vitamin D supplements are an effective treatment to reduce bone loss in the elderly. Most people can obtain adequate calcium in their diet but supplements are an alternative for people who find this difficult. Calcium alone has a limited effect as a treatment for osteoporosis but combined with vitamin D, it is particularly helpful for the elderly and housebound who cannot obtain natural sunlight and may have a poor diet.

Calcitriol an active form of vitamin D given to post-menopausal women who have osteoporosis in the spine. Calcitriol improves the absorption of calcium from the gut, as calcium cannot be absorbed without vitamin D.

Calcitonin is a hormone made by the thyroid gland which prevents the cells that break down bone from working properly, improving the action of bone building cells. Calcitonin is presently the only other FDA approved treatment. The drug acts by slowing the rate of bone loss and relieves bone pain. However, drawbacks with calcitonin are that it must be injected daily, it can cause nausea and it is very expensive compared with estrogen replacement therapy. Currently, only one form, Salcatonin (Calsynar) is licensed for the treatment of post-menopausal osteoporosis.

Testosterone is a treatment for men who are deficient in the male sex hormone, but it can also increase bone density in men with osteoporosis who have normal testosterone levels. It is available as injections or implants.

Anabolic steroids can increase bone and muscle mass and may be helpful in the very elderly who are frail and also in people with spinal fractures. Injections are carefully monitored due to side effects.

SERMs (Selective Estrogen Receptor Modulators) are a new generation of synthetic hormone replacement which reduce the risk of osteoporosis and heart disease, but do not increase the risk of breast or endometrial cancers. One form, raloxifene, is licensed for the prevention and treatment of osteoporosis in post-menopausal women.

Although there are a variety of osteoporosis therapies, there is a continuing need and a continuing search in this field of art for alternative osteoporosis therapies. The present invention seeks to fill that need.

SUMMARY OF THE INVENTION

It has been discovered, surprisingly, according to the present invention, that it is possible to treat osteoporosis, especially in post-menopausal women and men with low androgen levels, by administration of low dosages of an polysulfated polysaccharide compound capable of maintaining the integrity of bone, for example calcium pentosan polysulfate, polysulfated chondroitin and dextran polysulfate.

In one aspect, the present invention provides a method for the treatment of osteoporosis, comprising administering to a patient in need of such treatment, an effective amount of a polysulfated polysaccharide compound capable of maintaining the integrity of bone, for example calcium pentosan polysulfate, optionally with a pharmaceutically acceptable carrier, and optionally with at least one further compound selected from the group consisting of a bisphosphonate such as Fosamax, estrogen, calcium supplements, vitamin D supplements, calcitriol, calcitonin, testosterone, anabolic steroids, and SERMs (Selective Estrogen Receptor Modulators).

The compound is administered in an amount such as to produce a concentration of the compound in the blood of 0.01 to 100 micrograms/ml plasma, for example 0.1 to 50 micrograms per ml plasma. Typically, administration of about 5–20 mg/kg body weight of the compound will produce a plasma concentration in the range of 0.1–100 micrograms/ml.

In another aspect, the invention provides for use of a polysulfated polysaccharide compound capable of maintaining the integrity of bone in the treatment of osteoporosis.

In a further aspect, the invention provides pharmaceutical compositions suitable for use in the treatment of osteoporosis, comprising an effective amount of a polysulfated polysaccharide compound capable of maintaining the integrity of bone and at least one further compound selected from the group consisting of a bisphosphonate such a Fosamax, estrogen, calcium supplements, vitamin D supplements, calcitriol, calcitonin, testosterone, anabolic steroids, and SERMs (Selective Estrogen Receptor Modulators). The composition may optionally also comprise a pharmaceutically active carrier.

A surprising observation according to the present invention is that treatment of mammals with high repeated dosages of polysulfated polysaccharides, such as pentosan polysulfate causes bone fragility, whereas treatment with low dosages of polysufated polysaccharides, such as calcium pentosan polysulfate, in amounts producing blood levels in the range of 0.01 to 100 micrograms per ml on a low continuous or high pulsed therapy dose, reduces the occurrence or spread of osteoporosis by stimulating new bone growth directly or indirectly.

DETAILED DESCRIPTION OF THE INVENTION

It has been discovered, surprisingly, according to the present invention, that it is possible to effectively treat osteoporosis by administration of low dosages of a compound capable of maintaining the integrity of bone. Examples of such compounds are polysulfated polysaccharides, polysulfated dextran, polysulfated cyclodextran, polysulfated chondroitin, and pentosan polysulfate as its alkali metal or alkaline earth metal salt, for example its calcium or sodium salt, transition metals such as copper and zinc and noble metals such as platinum. Further examples are polysulfated polysaccharide derivatives of homopolysaccharides or heteropolysaccharides, which can be linear or branched . The sugars may come from but are not limited to pentoses or hexoses such as galactose, mannose, glucose, rhanose, fructose, sorbose, xylose, D-arabinose, ribose, L-arabinose, glucuronic acid and their derivatives.

The compound may be administered to the patient alone or in combination with a pharmaceutically acceptable carrier. Examples of such carriers are water and methyl cellulose.

Arteparon.RTM. (trade mark of Luitpold-Werk) consists predominantly of polysulfated chondroitin. It has been used as an anti-arthritic drug. More specifically, it is a heterogeneous semi-synthetic glycosaminoglycan polysulfate in which the predominant (about 93%) disaccharide repeating unit is hexuronic acid glycosidically linked to galactosamine. Approximately four of the free hydroxyl groups of the disaccharide repeating unit of Arteparon are esterified by sulfate groups to give a sulfur content of about 13.0% by weight. The commercial preparation has a molecular weight of about 10,000 Daltons.

Pentosan polysulfate as its calcium or sodium salt has an average molecular weight of about 5700 Daltons and a sulfur content of about 16%. This compound has been known since the early 1960s to be a synthetic heparinoid and an anti-thrombotic agent. The structural formula is shown in FIG. 1.

The preferred method of administration according to the method of the invention is by the oral route. Parenteral administration may also be employed, such as by way of injection iv or im, or subcutaneously. In such cases, the carrier would typically be normal sterile physiological saline.

The particular complexing ions may be selected from the group consisting of the alkali metals, e.g. $Na^+$ and $K^+$, alkaline earth metals, e.g. $Ca^{2+}$, $Zn^{2+}$, $Mg^{2+}$, $Ba^{2+}$, as well as $Ag^+$, $Au^+$, $Pb^{2+}$, $Cu^{2+}$, $Au^{2+}$, $Pd^{2+}$, $Pd^{4+}$, $Pt^{4+}$, $Pt^{2+}$, trivalent metal ions, and quaternary ammonium compound complexes. Examples of the latter compounds are pyridinium chloride, tetraalkyl ammonium chloride, choline chloride, cetylpyridinium chloride, N-cetyl-N,N,N-trialkylammonium chloride or their derivatives. The most preferred of these is the calcium complex.

Preparation of the polysulfate polysaccharide-metal complexes is described in detail in U.S. Pat. No. 5,668,116, the entire disclosure of which is incorporated herein by reference.

In another aspect, the invention provides novel pharmaceutical compositions suitable for use in the treatment of osteoporosis, the compositions comprise an effective amount of a polysulfated polysaccharide compound capable of maintaining the integrity of bone and at least one further compound selected from the group consisting of a bisphosphonate such a Fosamax, estrogen, calcium supplements, vitamin D supplements, calcitriol, calcitonin, testosterone, anabolic steroids, and SERMs (Selective Estrogen Receptor Modulators). The composition may optionally also comprise a pharmaceutically active carrier.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for treating osteoporosis in a mammal in need of such treatment, comprising the step of administering to said mammal an effective amount of a polysulfated polysaccharide compound capable of treating osteoporosis.

2. A method according to claim 1, wherein said polysulfated polysaccharide is selected from the group consisting of a pentosan polysulfate and polysulfated chondroitin.

3. A method according to claim 1 wherein the compound is a pure divalent metal ion chelate of a polysulfate of xylan having glycosidically linked D-glucuronyl side chains with divalent metal ions chelated thereto wherein substantially all monovalent ions have been substituted by divalent metal ions being selected from the group consisting of $Ca^{2+}$, $Mg^{2+}$, $Cu^{2+}$ and $Zn^{2+}$.

4. A method according to claim 3, wherein the D-glucuronyl side chains are substituted in a ratio of 1:1 up to 1:20 with xylan.

5. A method according to claim 3, wherein the metal ion is $Cu^{2+}$ or $Zn^{2+}$.

6. A method according to claim 3, wherein the metal ion is $Ca^{2+}$ or $Mg^{2+}$.

7. A method according to claim 5, wherein the xylan polysulfate has an average molecular weight of 1,000 to 10,000 Daltons and a sulfur content of about 16%.

8. A method according to claim 6, wherein the xylan polysulfate has an average molecular weight of 1,000 to 10,000 Daltons and a sulfur content of 16%.

9. A method according to claim 6, wherein the metal ion is $Ca^{2+}$.

10. A method according to claim 1 wherein the compound is administered to produce a concentration in the blood of 0.01 to 100 micrograms per ml blood.

11. A pharmaceutical composition suitable for use in the treatment of osteoporosis, comprising an effective amount of a polysulfated polysaccharide compound capable of maintaining the integrity of bone and at least one further compound selected from the group consisting of a bisphosphonate, estrogen, calcium supplements, vitamin D supplements, calcitriol, calcitonin, testosterone, anabolic steroids, and selective estrogen receptor modulators.

12. A pharmaceutical composition according to claim 11, wherein said polysulfated polysaccharide is calcium pentosan polysulfate.

13. A pharmaceutical composition according to claim 11, wherein said bisphosphonate is alendronate sodium.

14. A pharmaceutical composition according to claim 11, and further comprising a pharmaceutically acceptable carrier.

15. A method for treating osteoporosis in a mammal in need of such treatment, comprising the step of administering to said mammal an effective amount of a pharmaceutical composition as claimed in claim 11.

16. A method for treating osteoporosis in a mammal in need of such treatment, comprising the step of administering to said mammal an effective amount of a pharmaceutical composition as claimed in claim 12.

17. A method for treating osteoporosis in a mammal in need of such treatment, comprising the step of administering to said mammal an effective amount of a pharmaceutical composition as claimed in claim 13.

18. A method for treating osteoporosis in a mammal in need of such treatment, comprising the step of administering to said mammal an effective amount of a pharmaceutical composition as claimed in claim 14.

19. A method for treating osteoporosis in a mammal in need of such treatment, comprising the step of administering to said mammal an effective amount of a pentosan polysulphate compound capable of treating osteoporosis.

20. A pharmaceutical composition suitable for use in the treatment of osteoporosis, comprising an effective amount of a pentosan polysulfate capable of maintaining the integrity of bone and at least one further compound selected from the group consisting of a bisphosphonate, estrogen, calcium supplements, vitamin D supplements, calcitriol, calcitonin, testosterone, anabolic steroids, and selective estrogen receptor modulators.

21. A method according to claim 1 wherein the compound is administered to produce a concentration in the blood of 0.1 to 100 micrograms per ml blood.

22. A method according to claim 1 wherein the compound is administered in an amount of about 5–20 mg/kg body weight.

23. A method for treating osteoporosis according to claim 18, wherein said administration is as a low continuous or high pulsed therapy dose.

* * * * *

UNITED STATES PATENT AND TRADEMARK OFFICE
CERTIFICATE OF CORRECTION

PATENT NO.    : 6,593,310 B1
DATED         : July 15, 2003
INVENTOR(S)   : Cullis-Hill It is certified that error appears in the above-identified patent and that said Letters Patent is hereby corrected as shown below:

Title page,
Item [57], ABSTRACT,
Please delete the abstract and replace by the new abstract as follows:
-- A method for treating osteoporosis which comprises administering to a mammal in need of such treatment an effective amount, typically in the range of 0.1 to 100 micrograms/ml plasma, of a compound capable of maintaining the integrity of connective tissue, for example pentosan polysulfate. --.

FIGURE 1
Structural formula of pentosan polysulfate (PPS) isolated from beechwood hemicellulose (Fagus silvatica). This Formula shows that the linear xylan (pentosan) backbone of pentosan polysulfate contains on average one 4-O-methyl-glucuronate side chain linked to the 2-position on every tenth xylose (pentose) ring. The calcium derivative of PPS (CaPPS) is when $R = SO_3\text{-}Ca\ +^1/_2$.

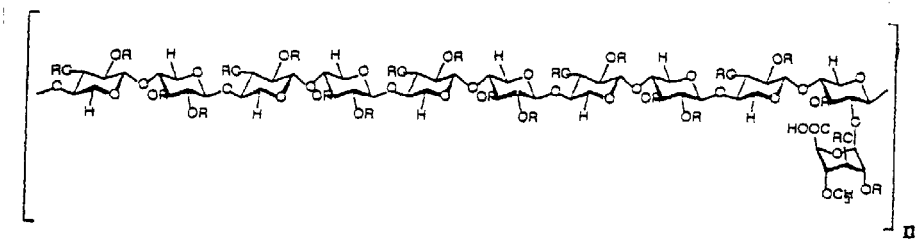

Signed and Sealed this

Thirty-first Day of August, 2004

JON W. DUDAS
*Director of the United States Patent and Trademark Office*